(12) United States Patent
Kunzler et al.

(10) Patent No.: US 7,276,619 B2
(45) Date of Patent: Oct. 2, 2007

(54) VITREORETINAL SILICONE TAMPONADES MADE BY SUPERCRITICAL FLUID EXTRACTION

(75) Inventors: Jay F. Kunzler, Canandaigua, NY (US); Joseph C. Salamone, Fairport, NY (US); Dharmendra Jani, Fairport, NY (US); Erik M. Indra, Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 511 days.

(21) Appl. No.: 10/801,741

(22) Filed: Mar. 16, 2004

(65) Prior Publication Data

US 2004/0176628 A1    Sep. 9, 2004

Related U.S. Application Data

(62) Division of application No. 10/165,834, filed on Jun. 7, 2002, now abandoned.

(60) Provisional application No. 60/366,696, filed on Mar. 21, 2002.

(51) Int. Cl.
C07F 7/02    (2006.01)
(52) U.S. Cl. .................................. 556/466
(58) Field of Classification Search ............... 556/466, 556/446
See application file for complete search history.

(56) References Cited

U.S. PATENT DOCUMENTS 5,336,487 A  *  8/1994  Refojo et al. ............ 424/78.04
5,340,614 A      8/1994  Perman
5,441,989 A      8/1995  Meinert
6,071,439 A      6/2000  Hahn
6,228,394 B1     5/2001  Horhota
6,294,194 B1     9/2001  Horhota

FOREIGN PATENT DOCUMENTS

| EP | 0435328 A | 7/1991 |
| JP | 2-302437 A | 12/1990 |
| JP | 05-043699 | * 2/1993 |
| JP | 5-43699 A | 2/1993 |
| JP | 06-107796 | * 4/1994 |
| JP | 6-107796 A | 4/1994 |
| JP | 9-150002 A | 6/1997 |
| WO | WO98/07554 A1 | 2/1998 |

OTHER PUBLICATIONS

Kim, et al., "Phase behaviors and fractionation of polymer solutions in supercritical carbon dioxide," Journal of Supercritical Fluids, PRA Press (USA), vol. 13 (No. 1-3), p. 99-106, (Jun. 15, 1998).
Crisp, et al., *Effect of Silicone Oil Viscosity on Emulsification*, Arch Ophthalmol, vol. 105, Apr. 1987, pp. 546-549.

* cited by examiner

*Primary Examiner*—Rebecca Anderson
*Assistant Examiner*—Joseph R. Kosack

(57) ABSTRACT

A process for the purification of a silicone oil or fluid using neat supercritical carbon dioxide or a supercritical carbon dioxide mixture extraction to produce vitreoretinal silicone tamponades. The subject process is an economical, highly effective, reproducible, contaminant-free method by which unreacted relatively low molecular weight cyclic siloxanes and oligomers are removed from relatively high molecular weight silicone oil or fluid.

13 Claims, No Drawings

VITREORETINAL SILICONE TAMPONADES MADE BY SUPERCRITICAL FLUID EXTRACTION

CROSS-REFERENCE TO RELATED APPLICATIONS

This application is a divisional of 10/165,834 filed Jun. 7, 2002, now abandoned.

Priority is hereby claimed in the present nonprovisional application to Provisional Application Ser. No. 60/366,696 filed Mar. 21, 2002, in accordance with 37 CFR 1.78(a)(4).

FIELD OF THE INVENTION

The present invention relates to tamponades and particularly to silicone tamponades that are configured to be injected as a vitreous substitute in the retina of a patient's eye.

BACKGROUND OF THE INVENTION

Ocular tamponades are vitreous substitutes that are used to reposition the retina of an eye in instances where a reattachment is not achievable by natural healing or by laser coagulation. The purpose of a vitreous substitute is to provide long-term tamponade of the retina, i.e., exhibit an ideal pressure (force/area) to position and maintain the retina in place. Current commercially used tamponades include perfluorocarbon-liquids, balanced salt solutions, silicone oil or fluid and gases, such as air, sulfur hexafluoride ($SF_6$) and perfluorocarbons (PFCs). Silicone oil or fluid is the preferred tamponade in cases of severe retina detachment, where the tamponade is used six months or longer.

Silicone oil or fluid is prepared by a ring-opening polymerization of strained cyclic silicones. The final product consists of relatively high molecular weight silicone fluid and unreacted relatively low molecular weight cyclic siloxanes and oligomers. The unreacted relatively low molecular weight cyclics and oligomers are cytotoxic and have been implicated in an undesirable emulsification phenomenon that sometimes occurs in silicone-based fluids. Accordingly, the unreacted relatively low molecular weight cyclics and oligomers must be removed from the silicone fluid product to be useful as an ocular tamponade. The preferred current method of purifying relatively high molecular weight silicone oil, or silicone fluid, involves the use of a lengthy solvent extraction process whereby the silicone fluid is slowly added to a non-solvent, such as acetone, and allowed to separate. The unreacted low molecular weight cyclics and oligomers are soluble in the non-solvent or acetone phase. The unreacted low molecular weight cyclics and oligomers are thus removed with the non-solvent or acetone phase upon separation thereof from the high molecular weight silicone fluid. Once separated, the non-solvent phase with the low molecular weight cyclics and oligomers becomes an undesirable waste product of the purification method and requires disposal. Likewise, following purification, controls are necessary to ensure the final silicone oil or fluid product is free of non-solvent contamination.

Because of the noted shortcomings of the current, preferred method of silicone fluid purification to remove cytotoxic impurities therefrom, there is a need for a purification method that is effective, less time consuming, eliminates the potential for non-solvent residual contamination and lessens or eliminates non-solvent waste production.

SUMMARY OF THE INVENTION

The present invention is an economical, highly effective process for the purification of relatively high molecular weight vitreofluid silicone oils or fluids using carbon dioxide supercritical fluid (SCF) extraction. A fluid with its temperature and pressure simultaneously higher than its critical temperature and pressure is in the supercritical state. The most ubiquitous SCF, carbon dioxide, is a gas at ambient conditions. In a supercritical state, it is essentially a compressed, high density fluid. Carbon dioxide is relatively innocuous, economical, and non-reactive under most operating conditions. The density, solvent power or selectivity of a SCF is easily altered with relatively small changes in pressure or by addition of small amounts of an organic solvent. The change in carbon dioxide density with pressure at 35 degrees Celsius does not increase linearly with increasing pressure. Small changes in pressure produce large changes in density when operating close to the critical point. For example, at 83 bar the compressibility of carbon dioxide is high. At 700 bar, the compressibility of carbon dioxide is low. The advantages of using carbon dioxide SCF for purification of vitreofluid silicone oils or fluids is that it is economical, reproducible, contaminant-free and in most cases does not require the disposal of non-solvent waste. Carbon dioxide SCF extraction in accordance with the present invention has solvating powers comparable to those of the non-solvents currently used in the purification of relatively high molecular weight silicone oil or fluid.

Accordingly, it is an object of the present invention to provide a process for the purification of relatively high molecular weight silicone fluid.

Another object of the present invention is to provide a process for the purification of relatively high molecular weight silicone fluid that is economical.

Another object of the present invention is to provide a process for the purification of relatively high molecular weight silicone fluid that is reproducible.

Another object of the present invention is to provide a process for the purification of relatively high molecular weight silicone fluid that is contaminant-free.

Another object of the present invention is to provide a process for the purification of relatively high molecular weight silicone fluid for use as an ocular tamponade.

Still another object of the present invention is to provide a process for the purification of a relatively high molecular weight silicone fluid that lessens or eliminates the need for non-solvent waste disposal.

A further object of the present invention is to eliminate low molecular weight silicone oligomers and cyclics from relatively high molecular weight silicone fluid in order to lessen or eliminate emulsification of the relatively high molecular weight silicone fluid in ocular tamponade uses.

These and other objectives and advantages of the present invention, some of which are specifically described and others that are not, will become apparent from the detailed description and claims that follow.

DETAILED DESCRIPTION OF THE INVENTION

The present invention relates to a novel process for the purification of relatively high molecular weight silicone oil or fluid for use as an ocular tamponade. The purification process of the present invention is a novel, economical, highly effective, reproducible, contaminant-free process for removing relatively low molecular weight cyclics and oligomers from relatively high molecular weight silicone oil or fluid. The subject process utilizes supercritical carbon dioxide ($scCO_2$) fluid extraction to purify silicone fluid for use as an ocular tamponade. The supercritical carbon dioxide fluid has solvating powers comparable to those of organic solvents. Likewise, the solvating power of the supercritical carbon dioxide fluid is adjustable through variations in pressure and temperature, or by adding modifiers to form a mixture as discussed in more detail below. Examples of suitable modifiers include but are not limited to methanol, isopropanol, acetonitrile and acetone.

Using the process of the present invention, a 5,000 cps silicone oil tamponade was purified using supercritical carbon dioxide fluid extraction. The conditions of the supercritical carbon dioxide fluid extraction consisted of carbon dioxide at a pressure of approximately 3,000 pounds per square inch (psi), a temperature of approximately 55 degrees Celsius and a flow rate of approximately 52 gm per minute. Using said conditions, the relatively low molecular weight cyclics and oligomers were removed from the silicone fluid to a level below size exclusion chromatography (SEC) detection limits. More particularly, SEC showed the removal of relatively low molecular weight cyclics and oligomers with no change in the silicone fluid peak height. Similar results were obtained by extracting with supercritical carbon dioxide fluid containing 10 percent acetone.

The silicone oil tamponade purification process of the present invention is described in still greater detail in the examples that follow.

EXAMPLE 1

Extraction of Silicone Oil with Supercritical Carbon Dioxide Fluid

Polydimethylsiloxane (21.01 gm) sample was loaded into a 0.7 inch tube. The loaded tube was then placed in a 3.0 inch cup. The 3.0 inch cup with the sample was placed into an extraction vessel and a lid with a ¼ inch pipe attachment was placed on the extraction vessel. The lid was placed such that the ¼ inch pipe attachment was inside the 0.7 inch tube. The extraction vessel was then pressurized to 140 bar with carbon dioxide using bottom to top flow. The extraction vessel temperature was approximately 55 degrees Celsius in an oil bath of approximately 102 degrees Celsius. A flow of 26 gm per minute carbon dioxide was begun in the extraction vessel from the top to the bottom. After one hour and 37 minutes, an increased flow rate of 52 gm per minute carbon dioxide was begun. After one hour and fifty-three minutes, the extraction vessel pressure was increased to 207 bar. After a total of four hours, the flow of carbon dioxide was discontinued and the extraction vessel was depressurized.

| Initial weights: | Extraction vessel = | 231.46 gm |
| | Cup = | 217.73 gm |
| | Lid and pipe = | 339.64 gm |
| | Tube = | 60.96 gm |
| | Sample = | 21.01 gm |

TABLE 1

SCF Extraction Process Conditions Summary for Example 1:

| Initial Conditions: | |
| --- | --- |
| $CO_2$ rate: | approximately 55 gm/minute driven by cylinder pressure up to 55-60 bars |
| Vessel pressure: | 140 bars |
| Vessel temperature: | 55 degrees Celsius |
| Oil bath temperature: | 102 degrees Celsius |
| Process Conditions: | |
| $CO_2$ rate: | approximately 26 gm/minute |
| Vessel pressure: | 140 bars |
| Flow time: | 90 minutes |
| $CO_2$ rate: | approximately 52 gm/minute |
| Vessel pressure: | 140 bars |
| Flow time: | 16 minutes |
| $CO_2$ rate: | approximately 52 gm/minute |
| Vessel pressure: | 207 bars |
| Flow time: | 67 minutes |

EXAMPLE 2

Extraction of Silicone Oil with Supercritical Carbon Dioxide Fluid and Acetone

Polydimethylsiloxane (21.01 gm) sample was loaded into a 0.7 inch tube. The loaded tube was then placed in a 3.0 inch cup. The 3.0 inch cup with the sample was then placed in an extraction vessel and a lid with a ¼ inch pipe attachment was placed on the extraction vessel. The lid was placed such that the ¼ inch pipe attachment was inside the 0.7 inch tube. The extraction vessel was then pressurized to 140 bar with carbon dioxide using bottom to top flow. The extraction vessel temperature was approximately 55 degrees Celsius in an oil bath of approximately 102 degrees Celsius. A flow of 6 gm per minute acetone and 20 gm per minute carbon dioxide was begun in the extraction vessel from the top to the bottom. After one and a half hours, 404.5 gm of acetone had been used. The flow of acetone was then discontinued while the flow of carbon dioxide was continued for an additional two and a half hours. The flow of carbon dioxide was likewise then discontinued and the extraction vessel was depressurized.

TABLE 2

SCF Extraction Process Conditions Summary for Example 2:

| Initial Conditions: | |
| --- | --- |
| $CO_2$ rate: | approximately 55 gm/minute driven by cylinder pressure up to 55-60 bars |
| Vessel pressure: | 140 bars |
| Vessel temperature: | 55 degrees Celsius |
| Oil bath temperature: | 102 degrees Celsius |
| Process Conditions: | |
| $CO_2$ rate: | approximately 20 gm/minute |
| Acetone rate: | 6 gm/minute |
| Pumping time: | 90 minutes |
| Vessel pressure: | 140 bars |
| Drying Conditions: | |
| $CO_2$ rate: | approximately 20 gm/minute |
| Acetone rate: | 0 gm/minute |
| Flow time: | 150 minutes |

CHART 1

Comparative Results for Silicone Oil Extracted by Various Processes

| Sample | Viscosity at 21° C. cps (mPa-s) | Surface tension, dynes/cm (mN/m) | Interfacial tension, dynes/cm (mN/m) |
|---|---|---|---|
| Silicone oil unextracted | 5,700 | 24.2 | Could not be measured |
| Acetone extracted silicone oil | 6,800 | 25.4 | Difficult to measure due to closeness of oil/water phase densities |
| sc-$CO_2$/acetone extracted silicone oil | 6,890 | 25.4 | 30 with distinct phases |
| sc-$CO_2$ extracted silicone oil | 8,000 | 25.4 | 32 with distinct phases |

Silicone oil or fluid ocular tamponades purified using the purification process of the present invention are used as customary in the field of ophthalmology. For example, in a surgical vitreoretinal procedure, the silicone oil or fluid ocular tamponade purified in accordance with the process of the present invention is placed and maintained in the posterior segment of the eye for the desired period of time prior to the removal thereof.

While there is shown and described herein a process for the purification of silicone oil or fluid for use as an ocular tamponade using supercritical carbon dioxide fluid or a supercritical carbon dioxide mixture fluid, it will be manifest to those skilled in the art that various modifications may be made without departing from the spirit and scope of the underlying inventive concept and that the same is not limited to particular processes herein described except insofar as indicated by the scope of the appended claims.

We claim:

1. A method of using a tamponade in an ophthalmic surgical procedure comprising:
   creating an incision into a posterior chamber of an eye; and
   filling said posterior chamber of the eye with said tamponade consisting essentially of a silicone oil that was purified by supereritical carbon dioxide extraction to remove cyclic and oligomeric impurities.

2. The process of claim 1 wherein said extraction is conducted at a pressure of approximately 3000 psi, and a temperature of approximately 55 degrees Celsius.

3. The process of claim 1 wherein said extraction is conducted at a carbon dioxide flow rate of approximately 20 to 26 gm/minute and a flow time of approximately 90 minutes.

4. A method of using a tamponade in an ophthalmic surgical procedure comprising:
   creating an incision into a posterior chamber of an eye; and
   filling said posterior chamber of the eye with said tamponade consisting essentially of a silicone oil that was purified with a mixture comprising carbon dioxide under supercritical extraction conditions to remove cyclic and oligomeric impurities.

5. The process of claim 4 wherein said extraction is conducted at a pressure of approximately 3000 psi, and a temperature of approximately 55 degrees Celsius.

6. The process of claim 4 wherein said extraction is conducted at a carbon dioxide mixture flow rate of approximately 20 to 26 gm/minute and a flow time of approximately 90 minutes.

7. The process of claim 4 wherein said carbon dioxide mixture comprises approximately 90 percent carbon dioxide and approximately 10 percent acetone.

8. The process of claim 4 wherein said carbon dioxide mixture comprises carbon dioxide and a modifier.

9. The process of claim 4 wherein said carbon dioxide mixture comprises carbon dioxide and acetone or acetonitrile.

10. The process of claim 4 wherein said carbon dioxide mixture comprises carbon dioxide and methanol.

11. The process of claim 4 wherein said carbon dioxide mixture comprises carbon dioxide and isopropanol.

12. The process of claim 4 wherein said carbon dioxide mixture comprises approximately 90 percent carbon dioxide and approximately 10 percent methanol.

13. The process of claim 4 wherein said carbon dioxide mixture comprises approximately 90 percent carbon dioxide and approximately 10 percent isopropanol.

* * * * *